(12) United States Patent
Upadhyay

(10) Patent No.: US 6,264,983 B1
(45) Date of Patent: Jul. 24, 2001

(54) DIRECTLY COMPRESSIBLE, ULTRA FINE ACETAMINOPHEN COMPOSITIONS AND PROCESS FOR PRODUCING SAME

(75) Inventor: Ajay Hasmukhlal Upadhyay, Avenel, NJ (US)

(73) Assignee: Rhodia, Inc., Cranbury, NJ (US)

( * ) Notice: Subject to any disclaimer, the term of this patent is extended or adjusted under 35 U.S.C. 154(b) by 0 days.

(21) Appl. No.: 09/397,356

(22) Filed: Sep. 16, 1999

(51) Int. Cl.$^7$ ........................................................ A61K 9/20
(52) U.S. Cl. ........................ 424/464; 424/465; 514/770; 514/772.3; 514/777; 514/778; 514/781; 514/784; 514/951
(58) Field of Search .................................... 424/489, 464, 424/465, 469, 470

(56) References Cited

U.S. PATENT DOCUMENTS

| | | | |
|---|---|---|---|
| 4,439,453 | 3/1984 | Vogel | 424/324 |
| 4,600,579 | 7/1986 | Salpekar et al. | 424/80 |
| 4,631,284 | 12/1986 | Salpekar et al. | 514/277 |
| 4,661,521 | 4/1987 | Salpekar et al. | 514/613 |
| 4,757,090 | 7/1988 | Salpekar et al. | 514/613 |
| 4,820,522 | 4/1989 | Radebaugh et al. | 424/468 |
| 5,073,380 | 12/1991 | Babu et al. | 424/472 |
| 5,370,878 | 12/1994 | Shah | 424/469 |

*Primary Examiner*—James M. Spear
(74) *Attorney, Agent, or Firm*—Ohlandt, Greeley, Ruggiero & Perle L.L.P.; George W. Rauchfuss, Jr.

(57) ABSTRACT

A directly compressible ultra fine acetaminophen granulation composition capable of being directly compressed into an acetaminophen tablet comprises from about 85 to about 95 wt % acetaminophen, from about 1 to about 4 wt % essentially water-insoluble tablet/capsule disintegrant, from about 0.5 to about 5.0 wt % polyvinylpyrrolidone, from about 0.5 to about 5.0 wt % totally pregelatinized starch, about 0.25 to about 3.0 wt % of a fluidizing agent, from about 0.25 to about 3.0 wt % of a lubricant, and optionally up to about 10 wt % of a co-active ingredient, the weight percents being based on the total weight of the dry components of the granulation composition, the granulation also comprising a moisture content of up to about 1.5 wt % based on the total weight of the dry components of granulation composition. This directly compressible acetaminophen granulation composition is produced by granulation in a top spray fluid bed granulator employing heated fluidization air, a first heated binder solution of a major portion of the polyvinylpyrrolidone dissolved in water, and a second binder solution of a minor portion of the polyvinylpyrrolidone and a portion of the totally pregelatinized starch and optionally a lubricant.

11 Claims, No Drawings

DIRECTLY COMPRESSIBLE, ULTRA FINE ACETAMINOPHEN COMPOSITIONS AND PROCESS FOR PRODUCING SAME

FIELD OF THE INVENTION

This invention relates to directly compressible ultra-fine acetaminophen (N-acetyl-p-aminophenol or APAP) compositions and to a process for preparing such ultra-fine compressible granulated compositions. The invention also relates to the preparation of tablets from such compositions. The invention also includes such ultra-fine APAP granulations alone or combined with other pro-active ingredients present in low quantity.

BACKGROUND OF THE INVENTION

Generally there are four methods in use in the United States for manufacture of tablets, namely direct compression, dry powder blend, pre-compressed dry powder blend and wet granulation, as explained in U.S. Pat. No. 4,439,453.

In the direct compression method, all the required tabletting ingredients (active and aids) are incorporated into a free flowing granulation which is supplied to the manufacturer of bulk tablets. The granulation requires no pre-processing or blending with additional aids in order to be tabletted. Rather, the free flowing granulation supplied to the tablet manufacturer can be charged directly to a tabletting press.

The direct compression method is a generally preferred method for a number of reasons including economical reasons. The analgesic aspirin is generally tabletted using such a direct compression method since crystalline aspirin is soft and exhibits good plasticity/elasticity when compacted into tablets.

However, because the analgesic acetaminophen has significantly different properties than aspirin, it is generally considered to be non-compressible and not readily amendable to production of directly compressible granulations thereof. Generally, the less desirable wet granulation method of tabletting has been used to tablet acetaminophen. Generally, these wet granulation processes require large amounts of excipients, e.g., from about 25 to about 40% or more by weight of excipients. That is, in contrast to aspirin, the acetaminophen crystals are hard and brittle and are easily fractured. The acetaminophen crystals have essentially no plasticity/elasticity and, therefore, have required the use of unduly large amounts of aids, lubricants and/or excipients in order to be compressible into tablets by the direct compression method.

Therefore, there is a recognized need for a direct tabletting granulated acetaminophen composition that is free flowing and capable of being directly compressible into tablets. A further need is for such a directly compressible acetaminophen granulation composition to provide a high load, for example, at least 80%, or preferably at least 90% or more, of acetaminophen active in the composition. Thus, the amount of excipients required in the compositions should be kept quite low, for example, 20% or less, preferably 10% by weight or less. In addition, the directly compressible acetaminophen composition should readily be free flowing and readily permit dry blending with other active ingredients should that be desired or required. A further need is that the directly compressible acetaminophen composition be such as to provide good flow and compressibility characteristics so as to produce tablets of content uniformity, acceptable hardness and friability, and also provide a fluid bed granulation with a characteristic rough surface morphology and a high surface area suitable for good blending potential with other co-actives.

SUMMARY OF THE INVENTION

This invention provides a directly compressible acetaminophen granulated composition. A directly compressible acetaminophen granulation composition of this invention and capable of being directly compressed into an acetaminophen tablet, comprises from about 80 to about 95 wt % acetaminophen, from about 1 to about 4 wt % essentially water-insoluble tabletcapsule disintegrant, from about 0.5 to about 5.0 wt % polyvinylpyrrolidone (povidone), from about 0.5 to about 5.0 wt % totally pre-gelantinized starch, about 0.25 to about 3.0 wt % of a fluidizing agent, and from about 0.25 to about 3.0 wt % of a lubricant, the weight percents being based on the total weight of the dry components of the granulation composition, the granulation also comprising a moisture content of up to about 1.5 wt % based on the total weight of the dry components of granulation composition.

The invention also comprises a process for producing such directly compressible acetaminophen granulation compositions. The process for the production of the directly compressible acetaminophen granulation compositions comprises: placing, as dry ingredients in a top spray fluid bed granulator, and dry blending with inert fluidization gas acetaminophen powder, the water-insoluble tablet/capsule disintegrant, a minor proportion of the totally pregelatinized starch, and at least a portion, or optionally all, of the fluidizing agent; heating the dry blend with heated pressurized fluidization gas, such as heated air, to fluidize and essentially uniformly heat the dry blend to a temperature in the range of about 25° C. to about 30° C.; when the dry blend has reached the desired temperature, spraying a first binder solution of a major portion of the polyvinylpyrrolidone dissolved in water from an atomizing spray gun of the granulation onto the heated dry blend to commence granulation of the dry powder blend; drying the granulation until the granulated product rises to about 2° C. above the end product temperature; spraying a second aqueous binder solution of the remaining minor portion of the polyvinylpyrrolidone, the remaining major portion of the totally pregelatinized starch, and optionally a lubricant, from an atomizing gun of the granulator onto the granulated product to further granulate and agglomerate the composition, and then drying this further granulated product until a moisture content of 1.5 wt % or less, preferably about 1.0 to 1.5 wt %, is achieved. The dried, directly compressible acetaminophen granulation composition, including APAP alone or in combination with other actives, is unloaded from the fluid bed granulator, and then can, if desired, be blended with other suitable dry ingredients in a suitable blender, to provide the directly compressible acetaminophen compositions of this invention.

The two spray process is necessary to effectively coat and agglomerate the ultra-fine particles to prepare fine particle sized granules having a high surface area and characteristic rough surface myphology suitable for good blending potential, content uniformity, tablet hardness and dissolution.

DETAILED DESCRIPTION OF INVENTION AND PREFERRED EMBODIMENTS

In the directly compressible composition of this invention, the ingredients thereof will generally be present in the following amounts expressed as percent by weight:

acetaminophen: 80 to 95%, preferably 87.5 to 92.5% tablet/capsule disintegrant: 1 to 4%, preferably 1.5 to 3.5% polyvinylpyrrolidone: 0.5 to 5%, preferably 2.75 to 3.25% pregelatinized starch: 0.5 to 5%, preferably 2 to 4% fluidizing agent: 0.25 to 3%, preferably 0.25 to 1.25% lubricant: 0.25 to 3%, preferably 0.25 to 1.25%.

The acetaminophen particles of the product are such that preferably a maximum of 30 wt % is retained on a 60 U.S. mesh screen, a maximum of 75 wt % is retained on a 100 U.S. mesh screen, a maximum of 95 wt % is retained on a 200 U.S. mesh screen, and a minimum of 80 wt % is retained on a 325 U.S. mesh screen.

The polyvinylpyrrolidone employed for its binding characteristics is preferably a lower molecular weight grade having an average molecular weight (Mw) of about 30,000 or less. As examples of grades of polyvinylpyrrolidone suitable for use in the invention, there can be mentioned povidone K30 or K29/32. Such polyvinylpyrrolidone impart a low viscosity to the binder solutions. A major amount of the polyvinylpyrrolidone is employed in the first binder solution as a particle coating agent, generally from about 80 to about 85 wt % of the total polyvinylpyrrolidone. The remaining minor amount of the polyvinylpyrrolidone, generally about 15 to 20 wt % of the total is employed in the second binder or agglomerating solution with a major amount, generally preferably about 65 wt % of the pregelatinized starch.

A minor portion of the pregelatinized starch, generally preferably about 35 wt % is used in the dry bowl charge to the fluid bed granulator as an intra-granular disintegrant, as well as a dry binder. The pregelatinized starch employed is totally pregelatinized starch, such as for example National Starch and Chemicals Corp. pregelatinized starch products 1551.

The total amount of the water-insoluble tablet/capsule disintegrant is used as a disintegrating agent in the dry bowl charge. The disintegrant is generally crosslinked sodium carboxymethylcellulose, sodium carboxylmethyl starch (also known as sodium starch glycolate), microcrystalline cellulose, soy protein, alginic acid, crosslinked polyvinylpyrrolidone (also known as crosslinked povidone), and mixtures thereof, but is preferably crosslinked sodium carboxymethylcellulose (croscarmellosee sodium).

Any suitable fluidizing agent may be employed in this invention, but preferably silicon dioxide is employed. This component is multifunctional and serves as a glidant, porosity reducer, granulation densifier and moisture scavenger, but primarily is employed as a fluidization aid during fluid bed granulation. Addition of the fluidizing agent to the initial dry charge to the fluid bed granulator helps the powders in the fluidized state for particle coating during the granulation process. Preferably at least about 50 wt % of the fluidizing agent is employed in the initial dry charge. Any remaining portion of the fluidizing agent not charged to the granulator in the dry charge can be blended with the product of the granulation process in a suitable blender to produce the final directly compressible composition.

Any suitable lubricant can be employed as the process of this invention, such as for example, stearic acid or mixtures of fatty acids, hydrogenated vegetable oils, triglycerides of fatty acids, metal stearates or metal salts of fatty acid mixtures, sodium lauryl sulfate, polyethylene glycol, talc, and mixtures of lubricants, but preferably stearic acid is employed. The lubricant can be added to the second binder solution or added in a dry form to the product of the granulation process by blending therewith in a suitable blender.

In preparing the first binder solution, the major portion of polyvinylpyrrolidone is dispersed and dissolved in water and heated to a temperature of about 50° C. to about 70° C., preferably to about 70° C. Heating of this binder solution before use in the granulation process provides improved spreading efficiency for coating onto the powder particles of acetaminophen to achieve good compressibility of the final product. Co-actives can also be incorporated into this first binder solution to ensure good content uniformity of the low dose co-actives.

In preparing the second binder solution, the remaining portions of polyvinylpyrrolidone and pregelatinized starch are dispersed in sufficient water and the solution heated to a temperature of from about 50° C. to about 70° C., preferably to about 70° C, to insure total gelatinization of the starch granules, as well as producing efficient spreading of the second binder solution on the granulation. Optionally, low melting fatty acid mixtures, such as stearic acid or hydrogenated vegetable oils, can be dispersed within the second binder solution. During granulation with the second binder solution, the particles agglomerate while building up particle size. However, other process variables maintain the fine particle size of the granulation.

The two-spray process of this invention is critical to effectively coat and agglomerate the particles, to prepare fine particle size granules having high surface area of from about 0.8 to about 1.0 m$^2$/g and characteristic "rough surface" morphology suitable for good blending potential, content uniformity, tablet hardness and dissolution.

Sufficient atomizing fluid (air) pressure is employed in the process to maintain a small droplet size for the binder solutions, and this in turn produces finer particle size in the resulting directly compressible granulated composition.

High fluidization air volume is required during fluidization of the powder. For example, in large scale manufacture of about 400 kg of granulated product, an air volume of between about 1800 to 3500 cfm is generally employed. Such large air volume keeps the particles sufficiently separated while permitting binder solution to spread on the particles in a way that keeps granule growth to a minimum, producing a finer particle size of the granulation. Preferably, a three-stage level in the air volume is employed in such a large scale manufacturing process. Initially a fluidization air volume of about 1800 cfm is employed. The air volume is then increased to about 2500 cfm about midway through granulation with the first binder solution, and then increased to about 3500 cfm at the beginning of the granulation with the second binder solution. This stepwise increase in fluidization air volume keeps the particles being granulated in a highly fluidized state to produce finer particle size of the granulated product composition, and keeps the fluidized state of granulation substantially constant even though the granule density keeps increasing from commencement to termination of the granulation process. The fluidization air employed is air heated to a temperature of at least 40° C., preferably at least about 50° C., and will generally be heated to within the range of from about 40° C. to 80° C., depending upon other process conditions including relative humidity.

Any suitable spray rate of binder solution may be employed in the process of this invention. In this previously mentioned large scale manufacturing process, a binder spray rate of from about 1700 to about 2400 g/min, preferably from about 1900 to about 2100 g/min, is employed.

By the process of this invention, a directly compressible acetaminophen composition can be provided that has a high loading of acetaminophen, preferably a load level of at least 90 wt % acetaminophen, and enables a tabletfer to produce tablets with the same dose of acetaminophen in each tablet.

The acetaminophen granulation produced by the process of this invention can be employed with low dose and other fine particle size active ingredients in tablets, such as for example, with psuedoephedrine hydrochloride, chlorpheniramine maleate, dextromethorphan hydrobromide, phenylpropanolamine hydrochloride, propoxyphen napsylate, hydrocodone, codeine phosphate and the like. The acetaminophen granulation of this invention can be blended with such other active ingredients in a simple mixing process and achieve good content uniformity of the other active ingredients in any resulting tablets formed by direct compression of the resulting blend.

The process of this invention can also incorporate other low dose co-active ingredients in the granulation charge, such as for example, those used in cough and cold medications and narcotic analgesic medications, used in amounts of up to about 10% by weight, generally from about 5 to about 10%. Co-actives of cough and cold remedies for analgesic, decongestant, antihistamine, cough suppressant combinations can include, for example, pseudoephedrine hydrochloride, dextromethorphan hydrobromide, phenylpropanolamine hydrochloride, chlorpheniramine maleate, and the like. Co-active narcotic analgesic medications can include, for example, propoxyphen napsylate, hydrocodone, codeine phosphate and the like. These co-actives can be incorporated in the granulation compositions produced by the process of this invention or can be blended with the resulting fine particle size granulation produced according to the process of this invention and achieve directly compressible granulation product having good content uniformity of the active ingredients.

The invention is illustrated, but not limited by, the following examples.

EXAMPLE 1

A laboratory-sized batch of directly compressible, ultra fine particle sized granulation of 90% acetaminophen was produced in a WSG-5 top spray fluidized bed granulator from Glaft GmbH of Germany.

The ingredients and their amounts employed in the dry charge and first and second binder solutions were as set forth in the following Table 1:.

TABLE 1

DRY BOWL CHARGE

| Ingredient | Amount (gm.) | % w/w |
|---|---|---|
| Acetaminophen | 6300.0 | 90.00 |
| Croscarmellose Sodium | 210.0 | 3.00 |
| Silicon Dioxide (Syloid 244FP) | 35.0 | 0.50 |
| Starch, pregelatinized | 84.5 | 1.21 |
| 1st Granulating Binder Solution | | |
| Povidone (K-30) | 175.0 | 2.50 |
| Water | 1770.0 | — |
| 2nd Granulating Binder Solution | | |
| Povidone (K-30) | 35.0 | 0.50 |
| Starch, pregelatinized | 150.0 | 2.14 |
| Stearic Acid | 10.5 | 0.15 |
| Water | 2225.0 | — |
| Grand Total (dry) | 7000.0 | 100% |

The granulating process conditions employed were as follows:

atomizing guns: single head, port size 1.8 mm, located 11" above granulator bowl

| | |
|---|---|
| atomizing air pressure | 3 bars |
| inlet temp. | 48–66° C. |
| product temp. | 25–29° C. |
| binder spray rate | 60 g./min. |
| process air volume | 240–1400 cfm |

The resulting granulation composition had a moisture content of 1.4%, a bulk density of 0.38 g/cc, and a flow rate of 6.7 g/sec. The particle size of the resulting granulation composition was:

| US Mesh | % Cum. Retained |
|---|---|
| 60 | 24.8 |
| 100 | 59.6 |
| 200 | 88.0 |
| 325 | 96.8 |

Directly compressible tablets from the resulting granulation composition were produced on a Manesty Betapress Series 16 (caplet tooling size 0.281"×0.687") of Manestary Machines, Ltd. of the UK. The properties of the directly compressed table produced were as set forth in Table 2.

TABLE 2

| Force-main (ton)/pre-(lb) | 0.5/— | 1/— | 1.5/— | 2/— | 2.5/— | 0.75/300 | 1/400 |
|---|---|---|---|---|---|---|---|
| Ejection (lb) | 70 | 90 | 90 | 90 | 90 | 80 | 90 |
| Weight (mg) | 549 | 551 | 550 | 546 | 551 | 551 | 552 |
| Hardness (SCU) | 9.6 | 16.6 | 14.2 | 13.6 | 13.3 | 12.8 | 17.0 |
| Thickness (inch) | 0.248 | 0.231 | 0.225 | 0.222 | 0.222 | 0.237 | 0.227 |
| Friability (%) | 0.49 | 0.35 | 0.69 | 0.86 | 0.78 | 0.47 | 0.33 |

EXAMPLE 2

A production-sized batch of directly compressible, ultra fine, particle sized granulation of 90% acetaminophen was produced in a GPCG-300 top spray fluidized bed granulator from Glatt GmbH of Germany.

The ingredients and their amounts employed in the dry charge and first and second binder solutions were as set forth in Table 3.

TABLE 3

DRY BOWL CHARGE

| Ingredient | Amount (km.) | % w/w |
|---|---|---|
| Acetaminophen | 360.0 | 90.00 |
| Croscarmellose Sodium | 12.00 | 3.00 |
| Silicon Dioxide (Syloid 244FP) | 2.00 | 0.50 |
| Starch, pregelatinized | 4.80 | 1.20 |
| 1st Granulating Binder Solution | | |
| Povidone (K-30) | 10.00 | 2.50 |
| Water | 101.0 | — |
| 2nd Granulating Binder Solution | | |
| Povidone (K-30) | 2.00 | 0.50 |
| Starch, pregelatinized | 8.60 | 2.15 |

TABLE 3-continued

DRY BOWL CHARGE

| Ingredient | Amount (km.) | % w/w |
|---|---|---|
| Stearic Acid | 0.60 | 0.15 |
| Water | 127.0 | — |
| Grand Total (dry) | 400.00 | 100% |

The granulating conditions employed were as follows:
atomizing guns: 6 head angle, port size 1.8 mm, located 34" above granulator bowl

| | |
|---|---|
| atomizing air pressure | 6 bars |
| inlet temp. | 64–71° C. |
| product temp. | 25–31° C. |
| binder spray rate | 2000–2400 g./min. |
| process air volume | 1800–3400 cfm |

The resulting granulation composition had a moisture content of 1.4%, a bulk density of 0.43 g/cc, and a flow rate of 6.8 g/sec. The particle size of the resulting granulation composition was:

| US Mesh | % Cum. Retained |
|---|---|
| 60 | 19.6 |
| 100 | 64.8 |
| 200 | 92.9 |
| 325 | 98.4 |

Directly compressible tablets from the resulting granulation composition were produced on a Manesty Betapress Series 16 as in Example 1. The properties of the directly compressed tablets produced were as set forth in Table 4.

TABLE 4

| Force-main (ton)/pre-(lb) | 0.5/— | 1/— | 1.5/— | 2/— | 2.5/— | 0.75/300 | 1/400 |
|---|---|---|---|---|---|---|---|
| Ejection (lb) | 90 | 120 | 120 | 120 | 120 | 120 | 120 |
| Weight (mg) | 553 | 554 | 556 | 555 | 556 | 555 | 556 |
| Hardness (SCU) | 10.6 | 15.9 | 17.0 | 14.2 | 13.3 | 13.8 | 16.1 |
| Thickness (inch) | 0.244 | 0.228 | 0.224 | 0.222 | 0.221 | 0.234 | 0.228 |
| Friability (%) | 0.62 | 0.41 | 0.41 | 0.49 | 0.54 | 0.51 | 0.45 |

EXAMPLE 3

Four individual production-sized batches of directly compressible, ultra fine particle sized granulations of 90% acetaminophen were produced on a GPCG-300 top spray fluidized bed granulator from Glaft GmbH. The four individual batches were then blended together in a 125 cu. ft. Gemco blender to produce a final directly compressible blend.

The ingredients and their amounts employed in the dry charge and first and second binder solutions to produce each individual batch were as set forth in Table 5.

TABLE 5

DRY BOWL CHARGE

| Ingredient | Amount (kg.) | % w/w |
|---|---|---|
| Acetaminophen | 360.0 | 89.69 |
| Croscarmellose Sodium | 10.00 | 2.49 |
| Silicon Dioxide (Syloid 244FP) | 2.00 | 0.50 |
| Starch, pregelatinized | 4.80 | 1.19 |
| 1st Granulating Binder Solution | | |
| Povidone (K-30) | 10.00 | 2.49 |
| Water | 101.0 | — |
| 2nd Granulating Binder Solution | | |
| Povidone (K-30) | 2.00 | 0.50 |
| Starch, pregelatinized | 8.60 | 2.14 |
| Water | 120.0 | — |
| Subtotal (dry) | 397.4 | |
| Post Granulation Dry Additives | | |
| Silicon Dioxide (Syloid 244FP) | 1.99 | 0.50 |
| Stearic Acid | 1.99 | 0.50 |
| Grand Total | 401.38 | 100% |

The granulating process conditions employed were as follows:
atomizing guns: 6 head angle, port size 1.8 mm, located 34" above granular bowl

| | |
|---|---|
| atomizing air pressure | 6 bars |
| inlet temp. | 58–80° C. |
| product temp. | 23–32° C. |
| binder spray rate | 1999–2102 g./min. |
| process air volume | 3000 cfm |

The resulting granulation composition of the blended individual batches has a moisture content of 1.4%, a bulk density of 0.45 g/cc, and a flow rate of 5.3 g/sec. The particle size of the blended granulation composition was:

| US Mesh Size | % Cum. Retained |
|---|---|
| 60 | 7.5 |
| 100 | 33.0 |
| 200 | 74.5 |
| 325 | 94.0 |

Directly compressible tablets from the blended granulation composition were produced on a Manesty Betapress Series 16 as in Example 1. The properties of the directly compressed tables produced were as set forth in Table 6.

TABLE 6

| Force-main (ton)/pre-(lb) | 0.5/— | 1/— | 1.5/— | 2/— | 2.5/— | 0.75/300 | 1/400 |
|---|---|---|---|---|---|---|---|
| Ejection (lb) | 20 | 30 | 30 | 30 | 30 | 25 | 30 |
| Weight (mg) | 557 | 556 | 557 | 556 | 556 | 556 | 556 |
| Hardness (SCU) | 9.6 | 14.8 | 12.0 | 12.6 | 11.9 | 12.5 | 15.6 |
| Thickness (inch) | 0.250 | 0.233 | 0.228 | 0.225 | 0.223 | 0.238 | 0.231 |
| Friability (%) | 0.63 | 0.34 | 0.83 | 0.97 | 1.01 | 0.45 | 0.41 |

EXAMPLE 4

A production-sized batch of directly compressible, ultra fine, particle sized granulation of 90.15% acetaminophen was produced in a GPCG-300 top spray fluidized bed granulator from Glatt GmbH of Germany and blended with dry additives in a 40 cu. ft. Gemco blender.

The ingredients and their amounts employed in the dry charge, first and second binder solutions, and dry additives were as set forth in Table 7.

TABLE 7

| DRY BOWL CHARGE | | |
|---|---|---|
| Ingredient | Amount (km.) | % w/w |
| Acetaminophen | 360.0 | 90.15 |
| Croscarmellose Sodium | 10.00 | 2.50 |
| Silicon Dioxide (Syloid 244FP) | 1.80 | 0.45 |
| Starch, pregelatinized | 4.80 | 1.20 |
| 1st Granulating Binder Solution | | |
| Povidone (K-30) | 10.00 | 2.50 |
| Water | 101.0 | — |
| 2nd Granulating Binder Solution | | |
| Povidone (K-30) | 2.00 | 0.50 |
| Starch, pregelatinized | 8.60 | 2.14 |
| Water | 120.0 | — |
| Post Granulation Dry Additives | | |
| Silicon Dioxide (Syloid 244FP) | 0.16 | 0.04 |
| Stearic Acid | 1.99 | 0.56 |
| Grand Total | 399.35 | 100% |

The granulating conditions employed were as follows:

atomizing guns: 6 head angle, port size 1.8 mm, located 34" above granular bowl

| atomizing air pressure | 5.6–5.7 bars |
|---|---|
| inlet temp. | 60–75° C. |
| product temp. | 30–38° C. |
| binder spray rate | 1713–1849 g./min. |
| process air volume | 1800–3500 cfm |

The resulting granulation composition had a moisture content of 1.3%, a bulk density of 0.40 g/cc, and a flow rate of 5.1 g/sec. The particle size of the resulting granulation composition was:

| US Mesh | % Cum. Retained |
|---|---|
| 60 | 11.0 |
| 100 | 51.5 |
| 200 | 89.5 |
| 325 | 98.0 |

Directly compressible tablets from the resulting granulation composition were produced on a Manesty Betapress Series 16 as in Example 1. The properties of the directly compressed tablets produced were as set forth in Table 8.

TABLE 8

| Force-main (ton)/pre-(lb) | 0.5/— | 1/— | 1.5/— | 2/— | 2.5/— | 0.75/300 | 1/400 |
|---|---|---|---|---|---|---|---|
| Ejection (lb) | 25 | 25 | 25 | 25 | 25 | 30 | 30 |
| Weight (mg) | 559 | 559 | 557 | 559 | 557 | 555 | 557 |
| Hardness (SCU) | 13.7 | 11.9 | 12.4 | 11.9 | 11.9 | 17.0 | 19.6 |
| Thickness (inch) | 0.238 | 0.230 | 0.225 | 0.223 | 0.222 | 0.229 | 0.226 |
| Friability (%) | 0.22 | 0.53 | 0.40 | 0.49 | 0.49 | 0.18 | 0.14 |

EXAMPLE 5

A laboratory-sized batch of directly compressible, ultra fine particle sized granulation of 90% acetaminophen with chlorpheniramine maleate co-active was produced in a WSG-5 top spray fluidized bed granulator from Glaft GmbH of Germany and blended with dry additives.

The ingredients and their amounts employed in the dry charge, first and second binder solutions, and any additives were as set forth in the following Table 9.

TABLE 9

| Ingredient | Amount (gm.) | % w/w |
|---|---|---|
| DRY BOWL CHARGE | | |
| Acetaminophen | 6300.0 | 90.00 |
| Croscarmellose Sodium | 149.3 | 2.13 |
| Silicon Dioxide (Syloid 244FP) | 35.0 | 0.50 |
| Starch, pregelatinized | 84.5 | 1.21 |
| 1st Granulating Binder Solution | | |
| Povidone (K-29/32) | 175.0 | 2.50 |
| Chlorpheniramine Maleate | 25.7 | 0.37 |
| Water | 2030.0 | — |
| 2nd Granulating Binder Solution | | |
| Povidone (K-29/32) | 35.0 | 0.50 |
| Starch, pregelatinized | 150.0 | 2.14 |
| Water | 2225.0 | — |
| Post Granulation Dry Additives | | |
| Silicon Dioxide (Syloid 244FP) | 35.0 | 0.50 |
| Stearic Acid | 10.5 | 0.15 |
| Grand Total | 7000.0 | 100% |

The granulating process conditions employed were as follows:

atomizing guns: single head, port size 1.8 mm, located 11" above granular bowl

| | |
|---|---|
| atomizing air pressure | 3.5 bars |
| inlet temp. | 50–73° C. |
| product temp. | 25–33° C. |
| binder spray rate | 62 g./min. |
| process air volume | 240–1400 cfm |

The resulting granulation composition had a moisture content of 1.1%, a bulk density of 0.39 g/cc, and a flow rate of 5.4 g/sec. The particle size of the resulting granulation composition was:

| US Mesh | % Cum. Retained |
|---|---|
| 60 | 13.6 |
| 100 | 50.0 |
| 200 | 84.4 |
| 325 | 96.8 |

Directly compressible tablets from the resulting granulation composition were produced on a Manesty Betapress Series 16 (caplet tooling size 0.281"×0.687") of Manestary Machines, Ltd. of the UK. The properties of the directly compressed tablets produced were as set forth in Table 10.

TABLE 10

| Force-main (ton)/pre-(lb) | 1/- | 1.5/- | 0.75/300 | 1/400 |
|---|---|---|---|---|
| Ejection (lb) | 120 | 120 | 120 | 120 |
| Weight (mg) | 557 | 557 | 556 | 555 |
| Hardness (SCU) | 17.4 | 19.8 | 14.3 | 17.7 |
| Thickness (inch) | 0.231 | 0.225 | 0.238 | 0.230 |
| Friability (%) | 0.49 | 0.49 | 0.50 | 0.59 |

EXAMPLE 6

A laboratory-sized batch of directly compressible, ultra fine particle sized granulation of 89.69% acetaminophen was produced in a WSG-5 top spray fluidized bed granulator from Glatt GmbH of Germany and blended with dry.

The ingredients and their amounts employed in the dry charge, first and second binder solutions, and dry additives were as set forth in the following Table 11.

TABLE 11

| Ingredient | Amount (gm.) | % w/w |
|---|---|---|
| DRY BOWL CHARGE | | |
| Acetaminophen | 6278.3 | 89.69 |
| Crosslinked polyvinylpyrrolidone (Crospovidone) | 174.3 | 2.49 |
| Silicon Dioxide (Syloid 244FP) | 35.0 | 0.50 |
| Starch, pregelatinized | 83.3 | 1.19 |
| 1st Granulating Binder Solution | | |
| Povidone (K-29/32) | 174.3 | 2.49 |
| Water | 1760.0 | — |
| 2nd Granulating Binder Solution | | |
| Povidone (K-29/32) | 35.0 | 0.50 |
| Starch, pregelatinized | 149.8 | 2.14 |
| Water | 2090.0 | — |
| Post Granulation Dry Additives | | |
| Silicon Dioxide (Syloid 244FP) | 35.0 | 0.50 |
| Stearic Acid | 35.0 | 0.50 |
| Grand Total | 7000.0 | 100% |

The granulating process conditions employed were as follows:

atomizing guns: single head, port size 1.8 mm, located 11" above granular bowl

| | |
|---|---|
| atomizing air pressure | 3 bars |
| inlet temp. | 55–70° C. |
| product temp. | 30–34° C. |
| binder spray rate | 60 g./min. |
| process air volume | 240–1400 cfm |

The resulting granulation composition had a moisture content of 1.4%, a bulk density of 0.37 g/cc, and a flow rate of 5.6 g/sec. The particle size of the resulting granulation composition was:

| US Mesh | % Cum. Retained |
|---------|-----------------|
| 60      | 25.2            |
| 100     | 62.8            |
| 200     | 88.4            |
| 325     | 97.6            |

Directly compressible tablets from the resulting granulation composition were produced on a Manesty Betapress Series 16 (caplet tooling size 0.281"×0.687") of Manestary Machines, Ltd. of the UK. The properties of the directly compressed tablets produced were as set forth in Table 12.

TABLE 12

| Force-main (ton)/pre-(lb) | 0.5/— | 1/—   | 1.5/— | 2/—   | 2.5/— | 0.75/300 | 1/400 |
|---------------------------|-------|-------|-------|-------|-------|----------|-------|
| Ejection (lb)             | 30    | 35    | 35    | 35    | 30    | 35       | 35    |
| Weight (mg)               | 555   | 557   | 556   | 554   | 555   | 558      | 558   |
| Hardness (SCU)            | 13.5  | 13.7  | 12.2  | 12.4  | 12.7  | 16.2     | 18.6  |
| Thickness (inch)          | 0.237 | 0.228 | 0.225 | 0.224 | 0.223 | 0.230    | 0.227 |
| Friability (%)            | 0.27  | 0.85  | 0.36  | 0.36  | 0.45  | 0.22     | 0.22  |

The surface area of the particles of each of the above-produced granulations of Examples 1 to 6, measured by BET methodology with more than ten points, was within the range of from about 0.80 to about 1.0 m$^2$/g.

With the foregoing description of the invention, those skilled in the art will appreciate that modifications may be made to the invention without departing from the spirit thereof. Therefore, it is not intended that the scope of the invention be limited to the specific embodiments illustrated and described.

What is claimed is:

1. A process for producing a directly compressible acetaminophen granulation composition comprising from about 80 to about 95 wt % acetaminophen, from about 1 to about 4 wt % essentially water-insoluble tablet/capsule disintegrant, from about 0.5 to about 5.0 wt % polyvinylpyrrolidone, from about 0.5 to about 5.0 wt % of totally pregelatinized starch, about 0.25 to about 3.0 wt % of a fluidizing agent, from about 0.25 to about 3.0 wt % of a lubricant, and optionally up to about 10 wt % of a co-active ingredient, the weight percents being based on the total weight of the dry components of the granulation composition, the granulation also comprising a moisture content of up to about 1.5 wt % based on the total weight of the dry components of granulation composition, said process comprising:
   (1) placing in a top spray fluid bed granulator and mixing with inert fluidization gas the acetaminophen, the water-insoluble tablet/capsule disintegrant, a minor portion of the totally pregelatinized starch, and at least a portion or optionally all of the fluidizing agent to produce a blend of dry ingredients;
   (2) introducing inert heated pressurized fluidization gas to substantially uniformly heat the blend of dry ingredients of step (1) to a temperature of from about 25° C. to about 30° C.;
   (3) providing to at least one atomizing gun of the top spray fluid bed granulator a heated first granulating binder solution of a major portion of the polyvinylpyrrolidone dissolved in water, and spraying the heated blend of dry ingredients of step (2) with the heated first binder solution;
   (4) drying the granulation product resulting from step (3);
   (5) providing to at least one atomizing air gun of the top spray fluid bed granulator a heated second granulating binder solution of the remaining minor portion of the polyvinylpyrrolidone and the remaining major portion of the totally pregelatinized starch, and optionally the lubricant, and spraying the dried granulation of step (4) with the heated second granulating binder solution; and
   (6) drying the granulation resulting from step (5) until the moisture content of the resulting granulation composition comprises from about 1.5 wt % or less, and blending therewith any of the fluidizing agent or lubricant not previously added.

2. A process according to claim 1 wherein the moisture content resulting from step (6) is from about 1.0 to about 1.5 wt %.

3. A process according to claim 2 in which the fluidizing agent is silicon dioxide and the lubricant is stearic acid, and the tablet/capsule disintegrant is selected from the group consisting of crosslinked sodium carboxymethylcellulose and crosslinked polyvinylpyrrolidone.

4. A process according to claim 2 wherein the acetaminophen of the composition comprises at least about 90 wt %.

5. A process according to claim 2 wherein the acetaminophen is finely divided particles of acetaminophen such that a maximum of 30 wt % is retained on a 60 U.S. mesh screen, a maximum of 75 wt % is retained on a 100 U.S. mesh screen, a maximum of 95 wt % is retained on a 200 U.S. mesh screen, and a minimum of 80 wt % is retained on a 325 U.S. mesh screen.

6. A process according to claim 3 wherein the acetaminophen comprises about 87.5 to about 92.5 wt %, the crosslinked sodium carboxymethylcellulose or crosslinked polyvinylpyrrolidone comprises from about 1.5 to about 3.5 wt %, the polyvinylpyrrolidone comprises from about 2.75 to about 3.25 wt %, the totally pregelatinized starch comprises from about 2.0 to about 4.0 wt %, the fluidized agent comprises from about 0.25 to about 1.25 wt % and the lubricant comprises from about 0.25 to about 1.25 wt %.

7. A process according to claim 1 wherein the granules of the granulation of step(6) have a surface area of from about 0.8 to about 1.0 m$^2$/g.

8. A process according to claim 5 wherein the granules of the granulation of step(6) have a surface area of from about 0.8 to about 1.0 m$^2$/g.

9. A process according to claim 1 wherein the first and second binder solutions are heated to a temperature of from about 50° C. to about 70° C.

10. A process according to claim 9 wherein the pressurized fluidization gas is introduced to the fluid bed granulator at a rate of about 1800 cfm during step (2), increased to a rate of about 2400 cfm during step (3), and further increased to a rate of about 3500 cfm during step (5).

11. A process according to claim 1 wherein the second binder solution includes a lubricant selected from a fatty acid or mixtures thereof.

* * * * *

UNITED STATES PATENT AND TRADEMARK OFFICE
CERTIFICATE OF CORRECTION

PATENT NO.   : 6,264,983 B1
DATED        : July 24, 2001
INVENTOR(S)  : Ajay Hasmukhlal Upadhyay It is certified that error appears in the above-identified patent and that said Letters Patent is hereby corrected as shown below:

Column 1,
Line 11, substitute -- co-active -- for "pro-active".

Column 3,
Line 56, (TABLE 3), substitute -- Amount (kg.) -- for "Amount (km.)".

Column 4,
Line 53, "tablefter" should be -- tabletter --.

Columns 5, 6, 7, 8, 9, 11 and 12,
In each of TABLES 1, 3, 5, 7, 9 and 11, the "Ingredient", "Amount" and "% w/w" subheadings should appear below each of the headings "DRY BOWL CHARGE", "$1^{st}$ Granulating Binder Solution" and "$2^{nd}$ Granulating Binder Solution", so that it is clear that "DRY BOWL CHARGE" is the heading for only the list of ingredient beginning with "Acetaminophen" and is not the heading for all of the ingredients listed the entire TABLE.

Column 6,
Line 26, substitute -- Manesty -- for "Manestary".
Line 28, "table" should be -- tablets --.

Column 7,
Line 5, (TABLE 3), substitute -- Amount (kg.) -- for "Amount (km.)".

Column 9,
Line 27, (TABLE 7), substitute -- Amount (kg.) -- for "Amount (km.)".

UNITED STATES PATENT AND TRADEMARK OFFICE
CERTIFICATE OF CORRECTION

PATENT NO.    : 6,264,983 B1
DATED         : July 24, 2001
INVENTOR(S)   : Ajay Hasmukhlal Upadhyay It is certified that error appears in the above-identified patent and that said Letters Patent is hereby corrected as shown below:

<u>Column 13,</u>
Line 12, substitute "Manesty" for "Manestary".

Signed and Sealed this

Ninth Day of July, 2002

*Attest:*

*Attesting Officer*

JAMES E. ROGAN
*Director of the United States Patent and Trademark Office*